United States Patent [19]
Nishiyama

[11] Patent Number: 5,875,899
[45] Date of Patent: Mar. 2, 1999

[54] APPARATUS FOR CLASSIFYING OBJECTS BY SEDIMENTATION

[75] Inventor: Yugo Nishiyama, Susono, Japan

[73] Assignee: Yazaki Corporation, Tokyo, Japan

[21] Appl. No.: 674,793

[22] Filed: Jul. 3, 1996

[30] Foreign Application Priority Data

Jul. 10, 1995 [JP] Japan ........................ 7-173337

[51] Int. Cl.⁶ .................................................. B03B 5/66
[52] U.S. Cl. .................. 209/156; 209/172; 209/173; 209/208
[58] Field of Search .................................. 209/156, 172, 209/172.5, 173, 208; 55/228, 233, 259, 421, 490, 492, 512, 527; 96/189, 219

[56] References Cited

U.S. PATENT DOCUMENTS 1,709,365  4/1929  Newsom .................................. 209/156

FOREIGN PATENT DOCUMENTS 6-328002  11/1994  Japan .
1565521  5/1990  U.S.S.R. ................................ 209/156

*Primary Examiner*—David H. Bollinger
*Attorney, Agent, or Firm*—Nikaido Marmelstein Murray & Oram, LLP

[57] ABSTRACT

In an apparatus for classifying objects by sedimentation having a straightening passage, capable of being prevented adhesion of bubbles to the straightening passage, and capable of being prevented a sample supplying error generated caused by a closed sample supplying portion on account of air locking, there is provided a bubble-removing passage for removing the bubbles within fluids at upper stream position of a straightening mesh within a classifying bath for classifying objects based on dropping position caused by a final sinking velocity of said objects falling within fluids after throwing said objects into flowing fluids, the bubble-removing passage which comprises a filter and a filter holder secured within the classifying bath through a protuberance.

11 Claims, 8 Drawing Sheets

FIG. 10 PRIOR ART

APPARATUS FOR CLASSIFYING OBJECTS BY SEDIMENTATION

BACKGROUND OF THE INVENTION

1. Field of the Invention

This invention relates to an apparatus for classifying objects by sedimentation, more particularly to an apparatus in which a classifying is performed by using final sedimentation velocity of objects to be classified mixed within fluid and there is provided a bubble-removing passage for removing bubbles within fluid of a classifying bath.

2. Description of the Prior Art

In conventional methods for classifying minute objects of powdery particles, it has been used an apparatus for classifying objects so as to classify the objects to make groups being different in size or density by use of the difference in their sedimentation velocity in fluid.

Figure 7:
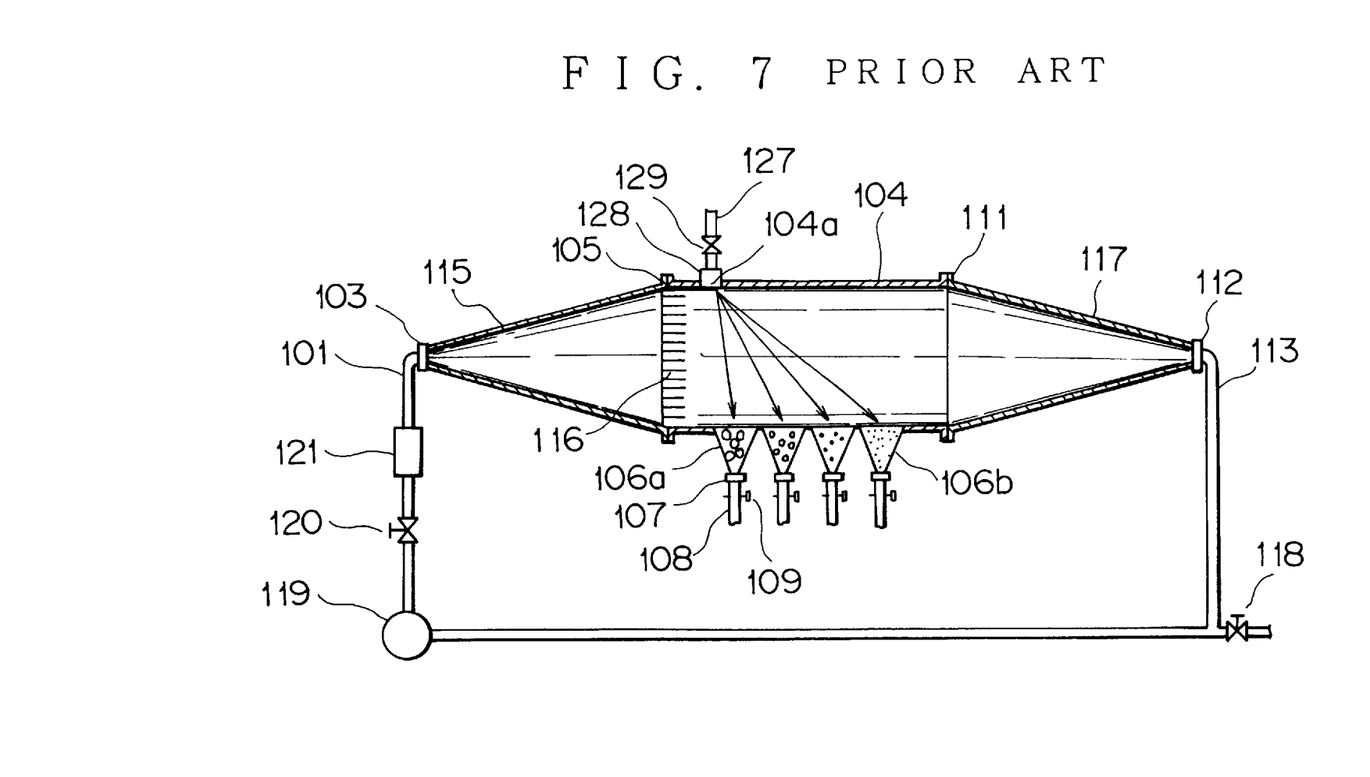
FIG. 7 is a schematic view showing a conventional apparatus for classifying objects by sedimentation.

FIG. 7 shows an example of an apparatus for classifying objects by sedimentation which has been disclosed in the Japanese Patent Application laid-Open No. 6-328002. In the drawing, a first cone-shaped pipe passage 115 is mounted on one side of an opening end of a classifying bath 104 through a flange 105 thereof. The first cone-shaped pipe passage 115 is gradually, widely opened toward the classifying bath 104 in the degree that the fluid does not become turbulence in the case of watching from the pointed end portion.

A second cone-shaped pipe passage 117 a tip 117a of which is opened, is mounted on the other opening end of the classifying bath 104 through the flange 105. The second cone-shaped pipe passage 117 is also gradually, widely opened toward the classifying bath 104 in the degree that the fluid does not become turbulence in the case of watching from the pointed end portion.

A pipe 101 is mounted detachably on the pointed end portion of the first cone-shaped pipe passage 115 and further a pipe 113 is also mounted on the pointed end portion of the second cone-shaped pipe passage 117. A drain 118, a pump 119, an amount of flowing adjusting valve 120, and a flowmeter 121 are arranged in sequence along the line from the pipe 113 to the pipe 101. A straightening lattice 116 is arranged in the neighborhood of the one opening end of the classifying bath 104. The straightening lattice 116 is arranged so as to avoid turbulence by straightening a fluid flowing therein from the first cone-shaped pipe passage 115. A throwing hole 104a is provided to throw objects to be classified therein at the upper part of neighboring said one opening end of the classifying bath 104 and a pipe 127 extending toward the vertical direction is connected to the throwing hole 104a. A boll valve 129 is arranged in the center part of the pipe 127, and a container (not illustrated), in which a suspension including minute objects of lumps of cells to be classified is accommodated, is connected to the upper end thereof.

A plurality of partitioning portions 106 (106a, 106b, . . . ) which narrow downward are provided at the lower part of the classifying bath 104. A respective half union 107 is connected to the lowest part of the partitioning portion 106.

An operation of the apparatus will be described as follows: The inside of the apparatus is filled with the fluid which is circulated within the apparatus by means of the pump 119. In the drawing, the fluid flows from left to right within the classifying bath 104.

In an example, the operation is explained in that the minute objects to be classified are lumps of cells, and fluid is culture. First, lumps of cells fall freely through the pipe 127 and are supplied to the classifying bath 104. At this time, in a relationship between density of culture as a fluid and that of lumps of cells, since density of lumps of cells is a little larger than density of culture accordingly, gravity, buoyancy and frictional resisting power which are subjected to lumps of cells immediately after falling, are in harmony with one another with the result that falling lumps of cells within the fluid promptly fall at the same velocity. This velocity is the final sinking velocity.

The lumps of cells reach the final sinking velocities before falling into the classifying bath 104 while falling through the pipe 127, from this time falling at the same velocity. The lumps of cells within the classifying bath 104 fall with drawing a line of oblique downward direction as shown in the drawing, then entering into the partitioning portion 106 (106a, 106b . . . ) at the lower part of the classifying bath 104, and being classified. At this time, the more lumps of cells have large configuration and have faster final sinking velocity, the more entering into the left partitioning portion 106a, and the more lumps of cells have small configuration and have slower final sinking velocity, the more entering into the right partitioning portion 106b. Thus the lumps of cells are capable of classifying selectively according to size or shape, namely the growing stage. The lumps of cells which enter each of the partitioning portion 106 are moved to the next stage passing through the tube 108 made of silicon.

Figure 8:
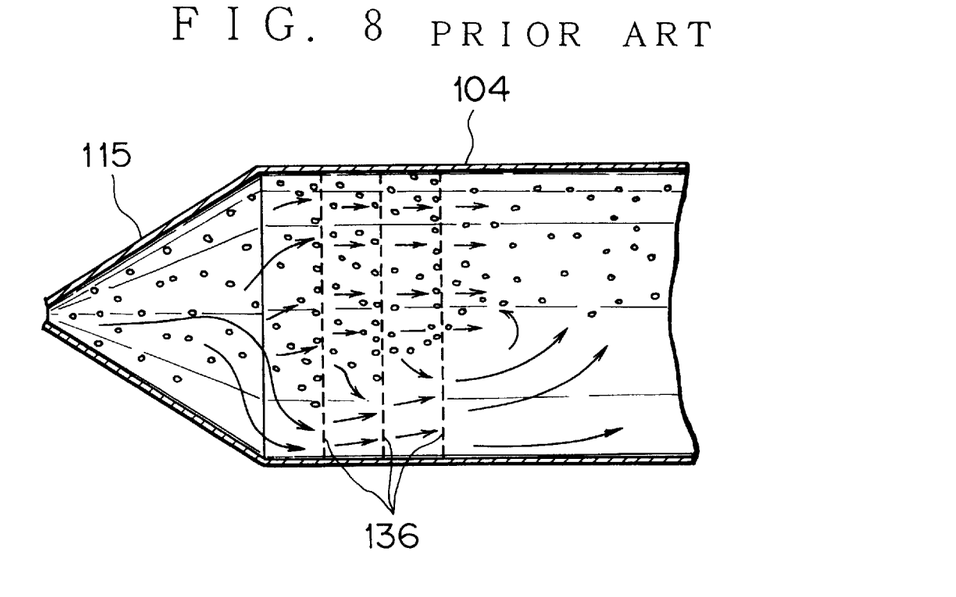
FIG. 8 is a cross sectional view showing an example of a straightening passage of the apparatus for classifying object by sedimentation.

In FIG. 8, a straightening mesh 136 which is of a mesh less than 5 mm degrees, is used rather than the straightening lattice 116 as the straightening passage of the classifying bath 104. In the drawing, three sheets of straightening meshes 136 are arranged at intervals.

Next, a sample supplying device for the conventional apparatus for classifying by sedimentation will be explained based on FIG. 9 and FIG. 10. In the same drawing, reference numeral 202 designates a classifying bath of the apparatus for classifying by sedimentation which is the same as the classifying bath disclosed in the above-stated Japanese Patent Application Laid-Open No. 6-328002. Besides, a sample supplying portion 201 is mounted on the upper portion of the classifying bath 202. The sample supplying portion 201 is formed in the shape of cylinder or polygonal cylinder. An outflow pipe 206 is mounted on the upper position of the sample supplying portion 201, an opening portion thereof is opened upside down. The other end of the outflow pipe 206 is reached within the culture fluid of the cultivating tank 203 through the pump 204 and a flow rate variable type pinch cock 207, and both of the outer flow pipe 206 and the sample inflow pipe 205 are filled with the same fluid as the culture fluid of the cultivating tank 203.

In the apparatus having above-described construction, cultivated lumps of cells which are cultivated within the cultivating tank 203, are forwarded with pressurization by means of pump 204 from a pointed end portion 205a to the sample supplying portion through the sample inflow pipe 205 together with the fluids including culture fluid. For this reason, upward flow is created within the sample supplying portion 201. The velocity of a flowing fluid thereof is adjusted by the pointed end portion 205, the inside diameter of the outflow tube 206, the sample supplying portion 201, the flow rate of pump 204 and the flow rate variable type pinch cock 207. The velocity of a flowing fluid thereof is adjusted in such a way that the velocity is a little faster than the sinking velocity of lumps of immature cultivated cells in the fluid.

Figure 10:
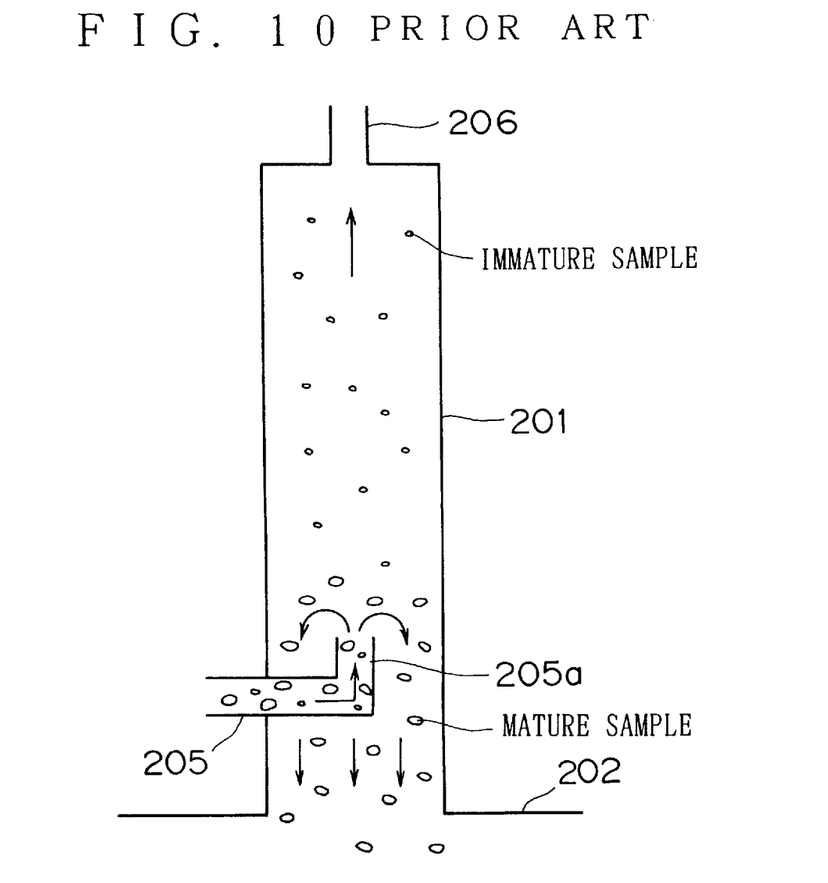
FIG. 10 is a cross sectional view showing a sample supplying portion of the sample supplying device of the apparatus for classifying objects by sedimentation of FIG. 9.

As shown in FIG. 10, therefore, only the immature samples flow upward in the sample supplying portion 201 to flow out into the outflow pipe 206, while, the sample to be classified may sink against the upward stream to come into the classifying tank 202. The immature samples having flown out from the outflow pipe 206 are returned to, via the pump 204 and the flow-rate variable type pinch cock 207, to the culture tank so as to be cultivated again.

However, in the conventional apparatus for classifying by sedimentation as described above, wherein at least one straigthening mess in which the meshes are less than 5 mm each is installed as the straightthening passage causing the classifying apparatus to operate with a laminar flow within the classifying bath, with air that is left in the classifying bath, the pipe, or the pump, extremely minute bubbles dispersed in the colloidal state within the fluid, and gas dissolved within the fluid becomes a visible mass of air with an elapse of time, and the mass of air is stirred by means of pump so that it becomes minute bubbles which flow into the classifying bath, as shown in FIG. 8. The minute bubbles cause clogging on account of adhesion thereof particularly on the upper portion of the fluid passage. As the result thereof, the velocity of fluid as is indicated by the arrow in the drawing, since the flow rate of the upper portion of the classifying bath becomes slow, and the lower portion thereof becomes fast, it can not keep the laminar flow within the classifying bath, in some cases, the sample becomes incapable of classifying accurately.

Figure 9:
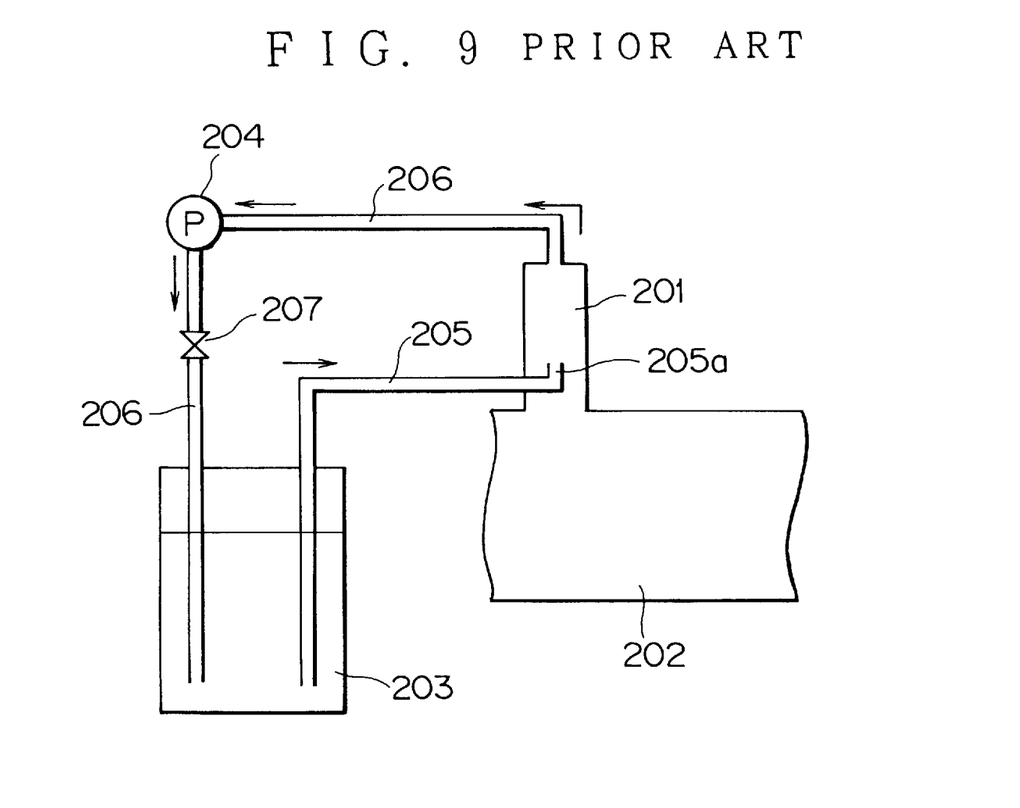
FIG. 9 is a schematic view showing a sample supplying device of a conventional apparatus for classifying objects by sedimentation.

Furthermore, the bubbles which have entered into the classifying bath collect at the upper portion thereof, entering into the sample supplying portion arranged at the upper part of the classifying bath as shown in FIGS. 9 and 10, the pipe of the sample supplying portion is closed by air lock and so forth, in some cases the samples become incapable of feeding therein.

SUMMARY OF THE INVENTION

In view of the foregoing, it is an object of the present invention to provide an apparatus for classifying objects by sedimentation in which there is provided a straightening passage therewith and it is capable of preventing adhesion of bubbles to the straightening passage, as well as capable of preventing a supplying error which is generated by the fact that the sample supplying portion is closed by air lock.

According to one aspect of the present invention, for achieving the above-mentioned object, there is provided an apparatus for classifying objects by sedimentation which has a classifying bath for classifying objects based on dropping position caused by a final sinking velocity of said objects falling within fluid after throwing said objects into flowing fluids comprising a bubble-removing passage for removing bubbles within said fluid provided within said classifying bath.

As stated above, as the apparatus for classifying objects by sedimentation according to the invention, there is provided a classifying bath with the bubble-removing passage capable of removing bubbles within the fluid of the classifying bath for classifying the objects.

The above and further objects and novel features of the invention will be more fully understood from the following detailed description when the same is read in connection with the accompanying drawings. It should be expressly understood, however, that the drawings are for purpose of illustration only and are not intended as a definition of the limits of the invention.

DETAILED DESCRIPTION OF THE PREFERRED EMBODIMENTS

A preferred embodiment of the invention will now be described in detail referring to the accompanying drawings.

Figure 1:
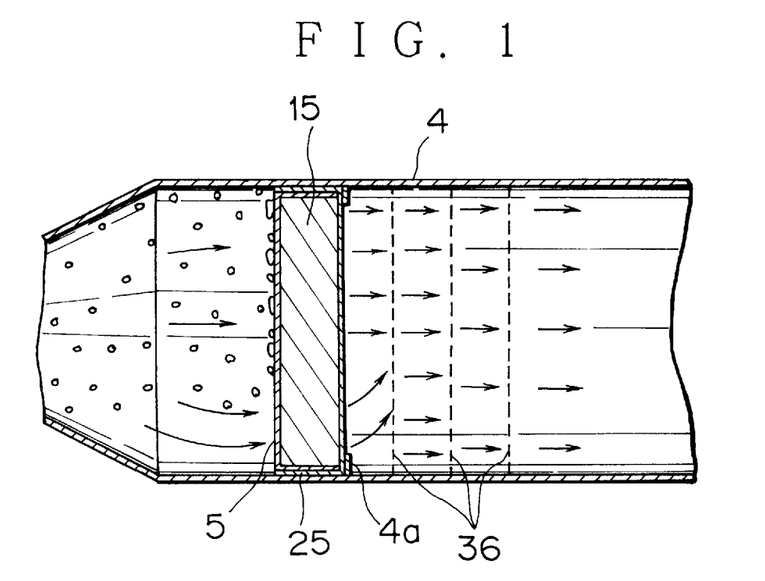
FIG. 1 is a cross sectional view showing a classifying bath in a first embodiment of an apparatus for classifying objects by sedimentation according to the present invention.

FIG. 1 is a cross sectional view which shows a classifying bath in the first embodiment of an apparatus for classifying objects by sedimentation according to the present invention. There is provided a bubble-removing passage 5 at an upper stream of the straightening meshes 136 (corresponding to reference numeral 36 in FIG. 1) as the straightening passage in the classifying bath 4 corresponding to the conventional classifying bath 104. Other structural components configuring the classifying bath and an apparatus for classifying objects by sedimentation are the same as the apparatus disclosed in the conventional example and Japanese Patent Application Laid-Open No. 6-328002 as shown in FIG. 8.

Figure 2A:
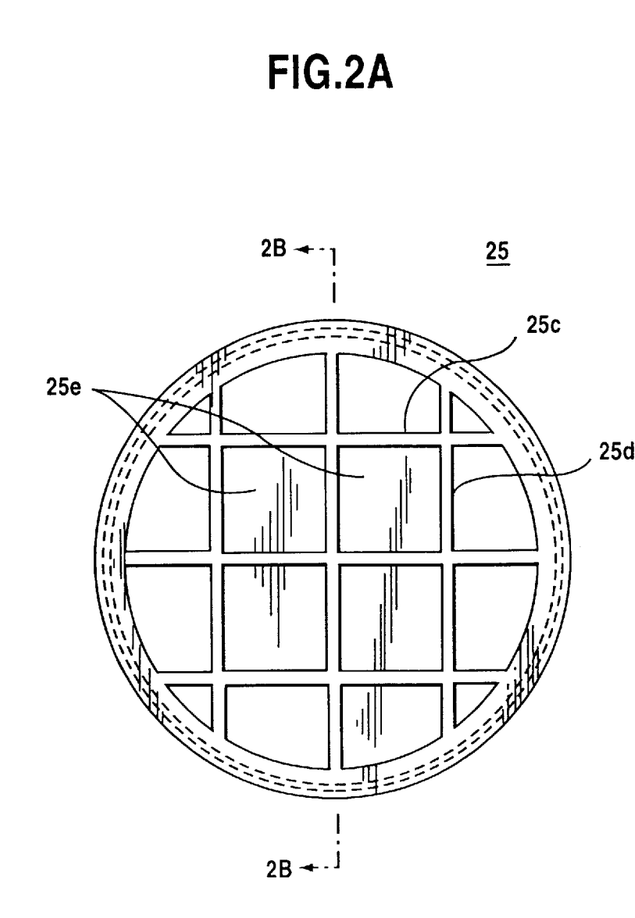
FIG. 2A is an elevation view showing a filter holder employed for the classifying bath of FIG. 1.
Figure 2B:
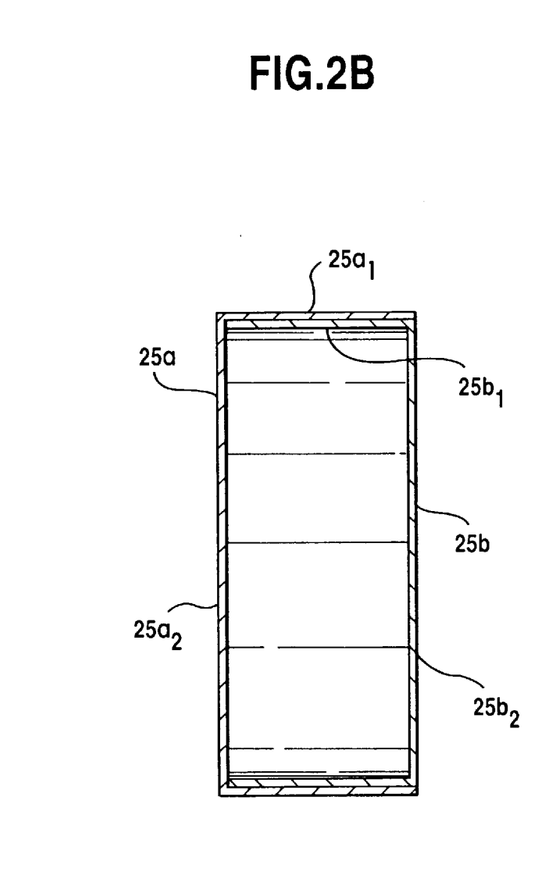
FIG. 2B is a cross sectional view along line I—I of FIG. 2A.

The bubble-removing passage 5 comprises a filter 15 and a filter folder 25. The filter holder 25 comprises two members 25a and 25b which are made of metal and have a U-shape sectionally surface. The two members 25a and 25b are overlapped as shown in FIG. 2A, and the filter 15 is arranged between both members 25a and 25b. Two surfaces 25a2 and 25b2 perpendicular to a stream of fluid of both members 25a and 25b are formed by a lateral directional member 25c and vertical directional member 25d having a lattice-shaped configuration as shown in FIG. 2A. In the opening part 25e composed of these members, there is constructed that the filter 15 is exposed so that the fluid comes into directly contact with the filter 15.

In mounting the filter holder 25 to the classifying bath 4, the opening end of the outer member 25a is arranged so as to be directed toward the upper stream portion of a stream of fluid so that the inner member 25b is inserted into the outer member 25a from the upper stream portion of the stream of the fluid. Furthermore, the outer periphery surface 25a1 of the outer member 25a is arranged so as to come into contact with an inner wall of the classifying bath 4, there is provided a ring shaped protuberance 4a for the inner wall of the classifying bath 4, an O-ring (not illustrated) and a seal-tape and so forth are provided between a side face of the upper stream portion of the protuberance 4a and a face 25a2 perpendicular to the stream of the fluid of the filter holder 25 so that it is capable of sealing completely even if the pressure of water pressure is added while the apparatus for classifying objects by sedimentation is operating. Furthermore, it is preferable that the filter holder 25 is capable of removing therefrom so that the filter holder 25 is capable of sterilizing as a whole.

The quality of the material for the filter 15 is of the material in which it is not corroded by a fluid to be used and not generating dust. In particular, when the classifying is performed under germ-free environment, using fiberglass, tetrafluoroethylene, cellulose acetate, nitrile cellulose, urethane and so forth all of which are capable of being performed high pressure sterilization by autoclaving or the like, or sterilization is capable of performing by an ultraviolet photoemission or a use of chemicals.

Next, an operation of the bubble-removing passage 5 for removing bubbles within the fluid according to this embodiment will be explained. In FIG. 1, the classifying bath 4 is filled with the fluid, and the direction of the stream of fluid is from left to right. The trashes such as bubbles are contained in the fluid before passing the bubble-removing passage 5 within the classifying bath 4. When the fluid reaches the bubble-removing passage 5, only the bubbles are separated by the filter 15 and adhere to the surface thereof. The bubbles adhered to the surface of the filter 15 grow with elapsing the operating time of the apparatus, in the course of time, the bubbles come up to upper part of the classifying bath 4. Then, the bubbles are extracted through the passage (not illustrated). As the result, no bubbles is existed completely in the fluid passed through the filter 15.

Figure 3:
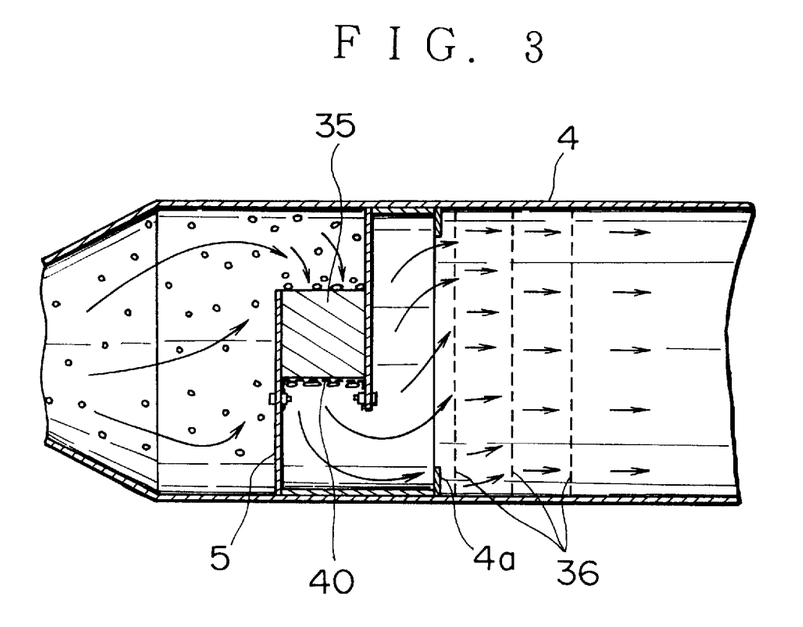
FIG. 3 is a cross sectional view showing a classifying bath in a second embodiment of an apparatus for classifying objects by sedimentation according to the present invention.
Figure 4A:
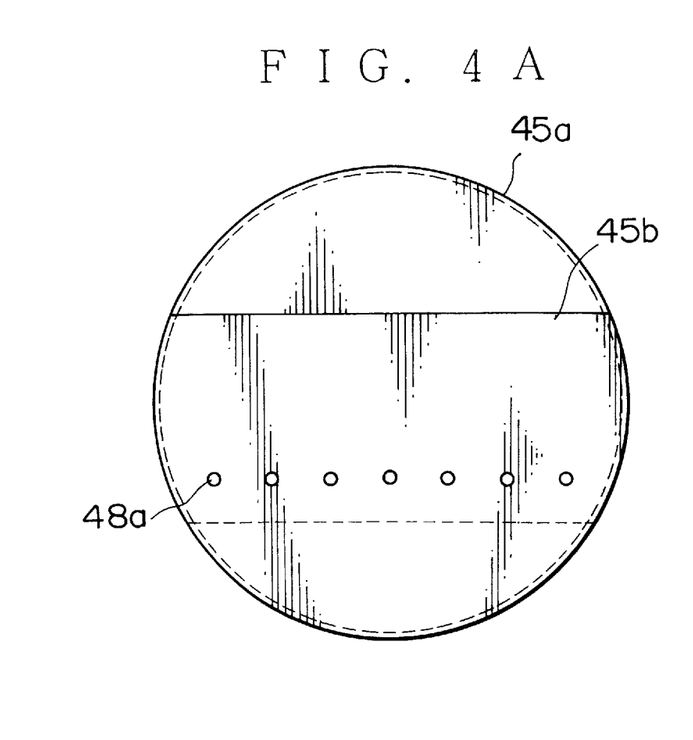
FIG. 4A is an elevation view showing a bubble-removing passage employed for the apparatus for classifying objects by sedimentation of FIG. 3.
Figure 4B:
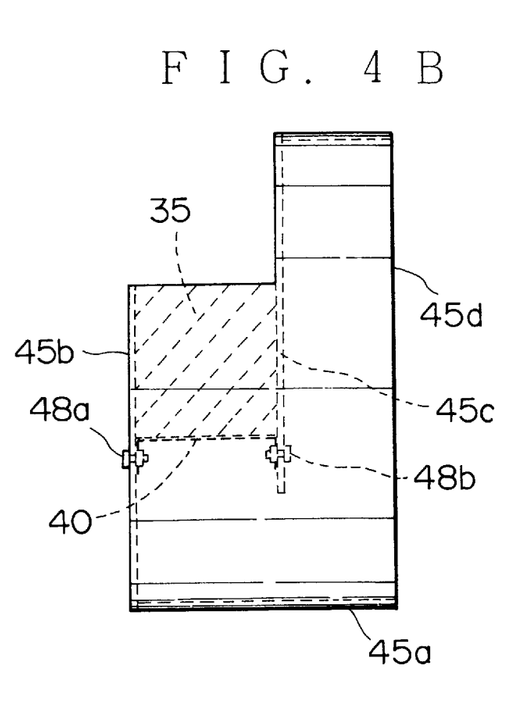
FIG. 4B is a side view of FIG. 4A.

Next, the second embodiment of the apparatus for classifying by sedimentation according to the present invention will be explained by using FIGS. 3 and 4. FIG. 3 is the cross sectional view showing the classifying bath according to the present embodiment. Just as described in the first embodiment, there is provided a bubble-removing passage 5 at an upper stream of the straightening meshes 136 (corresponding to reference numeral 36 in FIG. 3) as the straightening passage in the classifying bath 4 corresponding to the conventional classifying bath 104. Other structural components configuring the classifying bath and an apparatus for classifying by sedimentation are the same as the apparatus disclosed in the conventional example and Japanese Patent Application Laid-Open No. 6-328002 as shown in FIG. 8.

The bubble-removing passage 5 comprises a filter 35 and a filter holder 45. The filter holder 45 is composed of a cylindrical member 45a which comes into contact with an inner wall of the classifying bath 4 made of sterilizable synthetic resin as well as metal and D-shaped side boards 45b and 45c made of sterilizable synthetic resin as well as metal, being formed in such a way that the D-shaped side boards 45b and 45c are connected to the lower part and the upper part of the cylindrical members 45a respectively. The filter 35 is arranged between both the side boards 45b and 45c, a supporting net 40 is arranged at the lower part of the filter 35, the supporting net 40 is fixed to the side boards 45b and 45c by screws 48a and 48b. The filter 35 is formed a little larger than a filter mounting portion composed of both the side boards 45b and 45c of the filter holder 45, a front peripheral surface 45a and the supporting net 40 before mounting, in case mounting to the filter holder 45 causing the filter 35 to fix by pushing it into the filter mounting portion.

The side board 45b is arranged so as to look toward the upper stream portion of the flowing fluid. Further, the side board 45a of the filter holder 45 is arranged so as to come into contact with the inner wall of the classifying bath 4, a ring-shaped protuberance 4a is provided at the inner wall of the classifying bath 4, an O-ring or seal tape or the like (not illustrated) is provided between the side surface of the upper stream portion of the protuberance 4a and the peripheral surface of the downstream portion of the filter holder 45 so that the apparatus is capable of being constructed so as to seal completely even if the water pressure of the operating apparatus for classifying by sedimentation is added. Furthermore, it is preferable that the filter holder 45 is capable of removing therefrom so that the filter holder 45 is capable of sterilizing as a whole, the quality of the material for the filter 35 is the same as that of the above described the first embodiment.

Next, the operation of the bubble-removing passage 5 for removing the bubbles within the fluid according to the embodiment will be explained. In the starting time of the operation, the air is remained within the filter 35 of the inside of the classifying bath 4, when the fluid is flowed into the classifying bath 4, as shown in FIG. 3, the remained air within the filter 35 is pushed out so that it becomes relatively larger bubbles and collects at the lower part of the supporting net 40 with the result that the movement thereof toward the downstream is avoided by the side board 45c extending downward. Accordingly, the outflow of the bubbles is prevented at the starting time of operation.

Furthermore, just as the operation of the first embodiment described above, the classifying bath 4 is filled with the fluid, and the direction of the stream of fluid is from left to right. The trashes such as bubbles are contained in the fluid before passing the bubble-removing passage 5 within the classifying bath 4. When the fluid reaches the bubble-removing passage 5, only the bubbles are separated by the filter 35 and adhere to the surface thereof. The bubbles adhered to the surface of the filter 35 grow with elapsing the operating time of the apparatus, in the course of time, the bubbles come up to upper part of the classifying bath 4. Then, the bubbles are extracted through the passage (not illustrated). As the result, no bubbles is existed completely in the fluid passed through the filter 35.

Figure 5A:
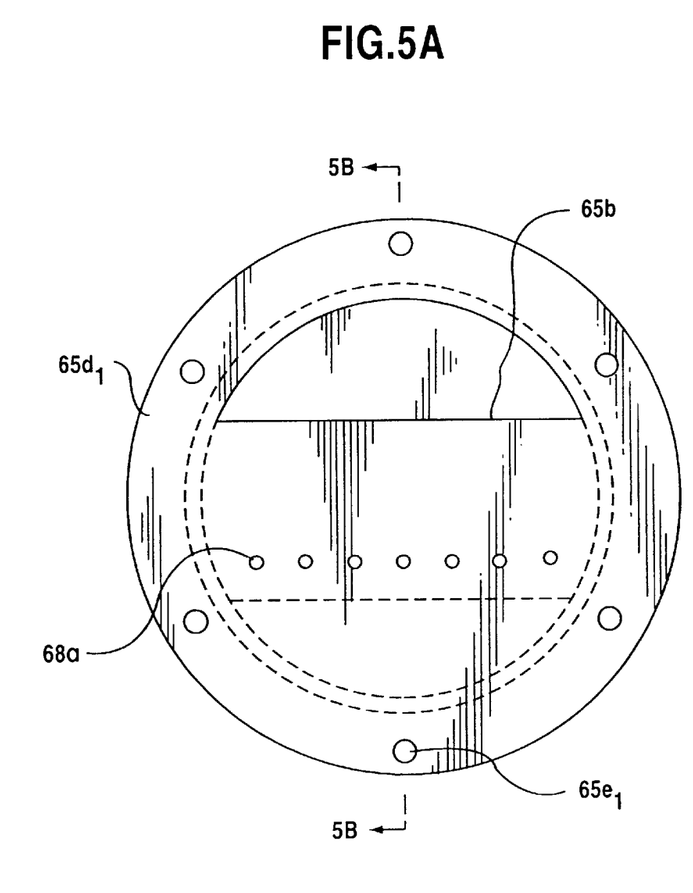
FIG. 5A is an elevation view showing a bubble-removing passage in a third embodiment of an apparatus for classifying by sedimentation according to the present invention.
Figure 5B:
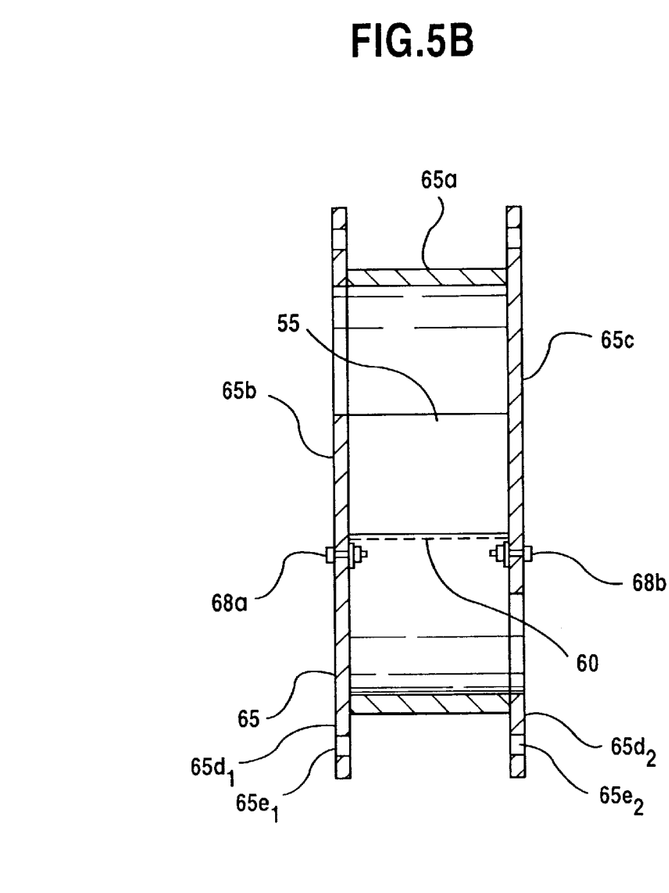
FIG. 5B is a cross sectional view along line II—II of FIG. 5A.

Next, the third embodiment of the apparatus for classifying objects by sedimentation according to the present invention will be explained based on FIGS. 5A and 5B. FIGS. 5A and 5B are elevation view and cross sectional view showing the bubble-removing passage 5 according to the embodiment. Just as described in the first embodiment and the second embodiment, there is provided a bubble-removing passage 5 at an upper stream of the straightening meshes 136 as the straightening passage in the classifying bath 4 corresponding to the conventional classifying bath 104. Other structural components configuring the classifying bath and an apparatus for classifying by sedimentation are the same as the apparatus disclosed in the conventional example and Japanese Patent Application Laid-Open No. 6-328002 as shown in FIG. 8.

The bubble-removing passage 5 comprises a filter 55 and a filter holder 65. As shown in FIG. 5B, the filter holder 65 is composed of a cylindrical member 65a made of invariable-geometric substance such as sterilizable synthetic resin as well as metal and D-shaped side boards 65b and 65c made of sterilizable synthetic resin as well as metal, being formed in such a way that the D-shaped side boards 65b and 65c are connected to the lower part and the upper part of the cylindrical members 65a respectively. The filter 55 is arranged between both the side boards 65b and 65c, a supporting net 60 is arranged at the lower part of the filter 55, the supporting net 60 is fixed to the side boards 65b and 65c by screws 68a and 68b.

A flange portion 65d1 is formed by a part of the side board 65b of the filter holder 65, and a flange portion 65d2 is formed by a part of the side board 65c. Furthermore, a plurality of locking holes 65e1 and 65e2 are pierced at the flange portions 65d1 and 65d2.

The side board 65b is arranged so as to look toward the upper stream of the flowing fluids in case of mounting the filter holder 65 on the classifying bath 4. Namely, in FIG. 5B, left side of the filter holder 65 is the upper stream portion and right side is the downstream portion. The left-side flange portion 65d1 of the filter holder 65 is secured by the screw at the flange (not illustrated) of corn-shaped pipe 115 as shown in FIG. 8, the right-side flange portion 65d2 of the filter holder 65 is secured by the screw at the flange (not illustrated) of the classifying bath 104, the filter holder 65 is arranged between the corn-shaped pipe 115 and a straightening mesh 136 of the classifying bath 104.

The operation for the bubble-removing passage 5 of the present embodiment is the same as above described for the second embodiment in that at the starting time of the operation, the air is remained within the filter 55 of the inside of the classifying bath 104, when the fluid is flowed into the classifying bath 104, the remained air within the filter 55 is pushed out so that it becomes relatively larger bubbles and collects at the lower part of the supporting net 60 with the result that the movement thereof toward the downstream is avoided by the side board 65c extending downward. Accordingly, the outflow of the bubbles is prevented at the starting time of operation.

Furthermore, In operation just as above-stated the second embodiment described above, the classifying bath 104 is filled with the fluid, and the direction of the stream of fluid is from left to right The trashes such as bubbles are contained in the fluid before passing the bubble-removing passage 5 within the classifying bath 104. When the fluid reaches the bubble-removing passage 5, only the bubbles are separated by the filter 55 and adhere to the surface thereof. The bubbles adhered to the surface of the filter 55 grow with elapsing the operating time of the apparatus, in the course of time, the bubbles come up to upper part of the classifying bath 104. Then, the bubbles are extracted through the passage (not illustrated). As the result, no bubbles is existed completely in the fluids passed through the filter 55. Moreover, in the present embodiment, the bubble-removing passage 5 is connected in series both to the corn-shaped pipe 115 and the classifying bath 104, accordingly the fluid passes invariably through the filter 55 with the result that the bubbles are capable of removing securely.

Figure 6A:
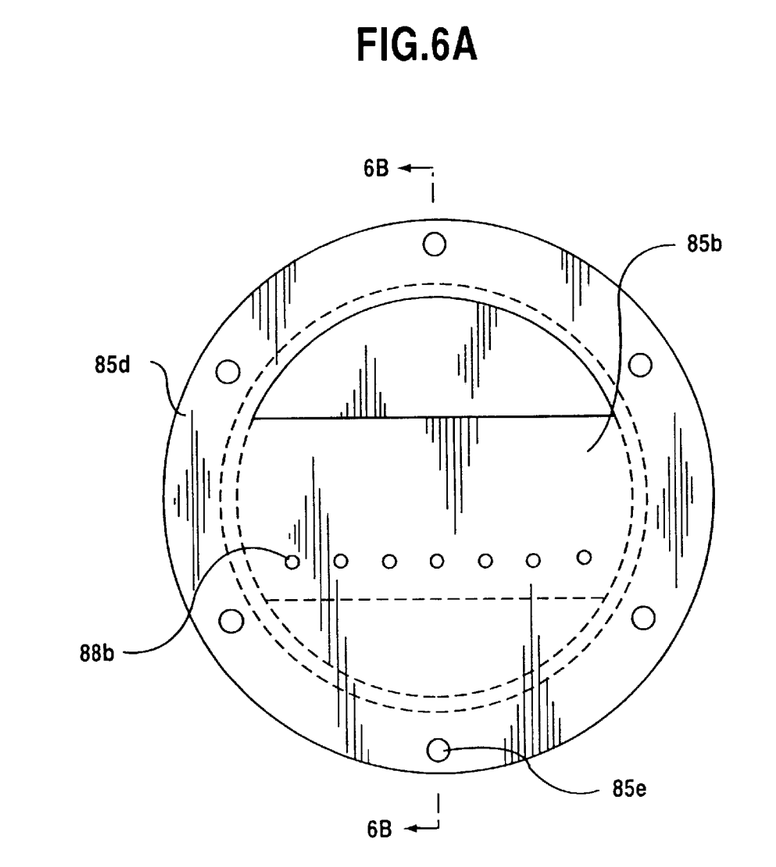
FIG. 6A is an elevation view showing a bubble-removing passage in a fourth embodiment of an apparatus for classifying objects by sedimentation according to the present invention.
Figure 6B:
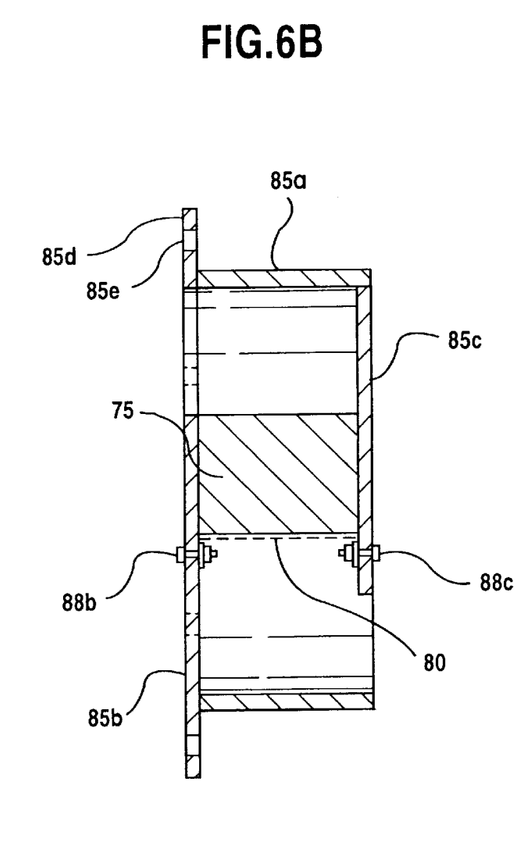
FIG. 6B is a cross sectional view along the line III—III of FIG. 6A.

Next, the fourth embodiment of the apparatus for classifying objects by sedimentation according to the present invention will be explained based on FIG. 6. FIG. 6 is the cross sectional view along the line III—III showing the bubble-removing passage 5 according to the present embodiment.

There is provided a bubble-removing passage 5 at an upper stream of the straightening meshes 136 as the straightening passage in the classifying bath 4 corresponding to the conventional classifying bath 104. Other structural components configuring the classifying bath and an apparatus for classifying by sedimentation are the same as the apparatus disclosed in the conventional example and Japanese Patent Application Laid-Open No. 6-328002 as shown in FIG. 8.

The bubble-removing passage 5 comprises a filter 75 and a filter holder 85. As shown in FIG. 6B, the filter holder 85 is composed of a cylindrical member 85a made of invariable-geometric substance such as sterilizable synthetic resin as well as metal and D-shaped side boards 85b and 85c made of sterilizable synthetic resin as well as metal, being formed in such a way that the D-shaped side boards 85b and 85c are connected to the lower part and the upper part of the cylindrical members 85a respectively. The filter 75 is arranged between both the side boards 85b and 85c, a supporting net 80 is arranged at the lower part of the filter 75, the supporting net 80 is fixed to the side boards 85b and 85c by screws 88b and 88c.

A flange portion 85d is formed by a part of the side board 85b of the filter holder 85. Furthermore, a plurality of locking holes 85e are pierced at the flange portion 85d.

The side board 85b is arranged so as to look toward the upper stream of the flowing fluids in case of mounting the filter holder 85 on the classifying bath 104. Namely, in FIG. 6B, left side of the filter holder 85 is the upper stream portion and right side is the downstream portion. A cylindrical member 85a of the filter holder 85 is fitted into inner wall of the classifying bath 104 (not illustrated) and the flange 85d is secured at the flange (not illustrated) of the classifying bath 104, mounting on the upper stream of the straightening mesh 136 of the classifying bath 104.

The operation for the bubble-removing passage 5 of the present embodiment is the same as above described the third embodiment in that at the starting time of the operation, the air is remained within the filter 75 on the inside of the classifying bath 104, when the fluid is flowed into the classifying bath 104, the remained air within the filter 75 is pushed out so that it becomes relatively larger bubbles and collects at the lower part of the supporting net 80 with the result that the movement thereof toward the downstream is avoided by the side board 85c extending downward. Accordingly, the outflow of the bubbles is prevented at the starting time of operation.

When the fluid reaches the bubble-removing passage 5, only the bubbles are separated by the filter 75 and adhere to the surface thereof. The bubbles adhered to the surface of the filter 75 grow with elapsing the operating time of the apparatus, in the course of time, the bubbles come up to upper part of the classifying bath 104. Then, the bubbles are extracted through the passage (not illustrated). As the result, no bubbles is existed completely in the fluid passed through the filter 75. Moreover, in the present embodiment, the bubble-removing passage 5 is connected in series the classifying bath 104 by the flange, accordingly the fluid passes invariably through the filter 75 with the result that the bubbles are capable of removing securely.

As stated above, since it is capable of being removed bubbles within the classifying bath for classifying the objects, with regard to the apparatus for classifying objects by sedimentation with straightening passage, adhesion of the bubbles is capable of being prevented, and there can be provided the apparatus for classifying objects by sedimentation which is capable of being prevented supplying error generated caused by closed sample supplying portion on account of the air lock.

While preferred embodiments of the invention have been described using specific terms, such description is for illustrative only, and it is to be understood that changes and variations may be made without departing from the spirit or scope of the following claims.

What is claimed is:

1. An apparatus for classifying objects by sedimentation comprising a classifying bath means for classifying objects based on different dropping positions of said objects falling with different final sinking velocities in a substantially horizontal flow of fluid, wherein said classifying bath means comprises an inner wall and a bubble-removing means located interior to said inner wall for removing bubbles within said fluid.

2. The apparatus according to claim 1, wherein said bubble-removing means comprises a filter and a filter holder.

3. The apparatus according to claim 2, wherein said filter is made of sterilizable fiberglass, tetrafluoroethylene, cellulose acetate, nitrite cellulose or urethane.

4. The apparatus according to claim 2, wherein
(A) said classifying bath means is a substantially horizontal cylinder having an axis therethrough,
(B) said filter holder comprises
    (1) a cylindrical member, which
        (a) comprises an inner wall and an axis, and
        (b) contacts the inner wall of said classifying bath means, with the axis of said cylindrical member at least substantially aligning with the axis of said classifying bath means; and
    (2) two side members, which side members are at least substantially perpendicular to the axis of said cylindrical member, each of said side members defining a port therethrough or between it and the inner wall of said cylindrical member with the two side members and their included ports cooperating to cause the fluid flowing through said cylindrical member to change flow direction when flowing between said side members to a direction more perpendicular to the axis of said cylindrical member, wherein said side members are generally connected to opposite areas of the inner wall of said cylindrical member; and
(C) said filter is located between said two side members, said filter having a down stream part comprising a supporting net fixed to said side members.

5. The apparatus according to claim 4, wherein the filter holder comprises two flange portions, each independently formed by one of said two side members.

6. The apparatus according to claim 5, wherein a plurality of locking holes are pierced at said flange portions.

7. The apparatus according to claim 4, wherein said side members are D-shaped side boards.

8. The apparatus according to claim 4, wherein the cylindrical member comprises a lower part and an upper part with one of said side members connected to the lower part and the remaining said side member connected to the upper part.

9. The apparatus according to claim 4 wherein said cylindrical member and/or said side members are made of a sterilizable synthetic resin and a metal.

10. The apparatus according to claim 1, wherein a ring-shaped protuberance is provided on the inner wall of said classifying bath means, which protuberance is situated downstream of said bubble-removing means and sealingly engages therewith.

11. The apparatus according to claim 10, wherein said protuberance is sealed against an abutting bubble-removing means by an O-ring or seal tape.

* * * * *